United States Patent [19]

Wong

[11] Patent Number: 4,828,830

[45] Date of Patent: May 9, 1989

[54] METHOD AND COMPOSITION FOR PROPHYLAXIS AND TREATMENT OF VIRAL INFECTIONS

[75] Inventor: Grace H. W. Wong, South San Francisco, Calif.

[73] Assignee: Genentech, Inc., South San Francisco, Calif.

[21] Appl. No.: 822,099

[22] Filed: Jan. 24, 1986

[51] Int. Cl.$^4$ .................. A61K 45/02; A61K 37/02
[52] U.S. Cl. .................. 424/85.5; 514/2; 424/85.1
[58] Field of Search .......... 424/85; 530/351; 435/68; 514/2

[56] References Cited

U.S. PATENT DOCUMENTS 4,495,282   1/1985   Ohnishi et al. .................. 435/68

FOREIGN PATENT DOCUMENTS

| 4841285 | 10/1985 | Australia . |
| 0110044 | 6/1984 | European Pat. Off. . |
| 0128009 | 12/1984 | European Pat. Off. . |
| 0131789 | 1/1985 | European Pat. Off. . |
| 0148311 | 7/1985 | European Pat. Off. . |
| 0168214 | 1/1986 | European Pat. Off. . |
| 0170843 | 2/1986 | European Pat. Off. . |
| 0209030 | 1/1987 | European Pat. Off. . |
| 2158829 | 11/1985 | United Kingdom . |

OTHER PUBLICATIONS

Merck Index-10th Edition, No. 4870 pp. 724-725.
Huygen et al., Eur. J. Clin. Microbiol. 4(3): 304-309 (1985).
Murray et al., J. Immunol. 135(4):2374-2377 (1985).
Fauci et al., Ann. Internal. Med. 100:92-106 (1984).
Gottlieb et al. in Gallin et al., Eds. "Advances in Host Defense Mechanisms" 5:149-170 (1985).
Nishida et al., Jpn. J. Cancer Res. 76(4):249-252 (1985).
Ho et al., The Lancet, Mar. 16, 1985, pp. 602-604.
Murray et al., New Eng. J. Med. 310(14):883-889 (Apr. 1984).
Pennington et al., J. Infect. Diseases 153(3):609-612 (1986).
Kleinerman et al., J. Clin. Oncology 3(7):1005-1012 (1985).
Klatzman et al., Nature 319:10-11 (1986).
Moore et al., New Eng. J. Med. 312(7):442-443 (1985).
Yamamoto et al., J. Interferon Res. 6:143-152 (1986).
Lane et al., Clin. Res. 32(2):351 A (1984).
Adams et al., J. Immunol. 127(5):1973-1977 (1981).
Weiss et al., J. Clin. Invest. 68:714-721 (1981).
Aderka et al., Cell. Immunol. 92:218-225 (1985).
Eifel et al., Cell. Immunol. 47:197-203 (1979).
Hayden et al., New Eng. J. Med. 314(2):71-75 (1986).
Babiuk et al., J. Gen. Virol. 66:2383-2394 (1985).
"A Seminar in Bovine Immunology" Western Veterinary Conf. Feb. 16, 1987.

*Primary Examiner*—Blondel Hazel
*Attorney, Agent, or Firm*—Max D. Hensley

[57] ABSTRACT

TNF or LT qualitatively and quantitatively potentiates the anti-viral activity of interferons, thus permitting the use of lower interferon doses to protect uninfected cells from interferon sensitive and relatively insensitive viruses and to selectively kill virus-infected cells.

8 Claims, 9 Drawing Sheets

Fig.1. EMC/A549 Cells

Fig. 2. VSV/MDBK Cells

Fig. 5A. EMC/A549

METHOD AND COMPOSITION FOR PROPHYLAXIS AND TREATMENT OF VIRAL INFECTIONS

BACKGROUND

This invention relates to the treatment of animals which have been virally infected or which are at risk for exposure to viral infection. In particular, it is concerned with inducing in mammalian cells a state of resistance to viral infection.

Interferons have been used to varying effect for the prophylaxis or treatment of chronic, acute and/or experimental infections by viruses such as vaccinia, rubella, herpes simplex, varicella-zoster, chicken pox, cytomegalovirus, adenovirus, ebola virus, rabies and hepatitis B. Chronic cytomegalovirus infections have proven difficult to treat by interferons, even using much higher doses than were needed than for the prevention of CMV infections; these doses may involve undesirable side reactions such as neutropenia and suppression of weight gain. Accordingly, it would be desirable in patients with persistent or chronic viral infections to provide an interferon preparation that is more efficacious without inducing interferon side-effects.

Interferons also have been widely tested for their ability to prevent or treat the common cold (primarily rhinovirus infections). Most studies have intranasally administered daily doses ranging from $0.8 \times 10^6$ to $42.8 \times 10^6$ units (Finter et al., 1985, *Interferon* Vol. 4 pp. 186–187). However, it should be understood that the relationship between the specific activities reported by early workers and the International Standards now in use is unclear; the dosages employed when expressed in International Units could have been greater or lower. Intranasal administration generally was as an aerosol, although delivery by soaked pledget has been reported as more efficacious. Typically, the daily dosage is aliquoted and administered 1 to 3 times per day. Experience with recombinant interferons has shown that sprays delivering about $1 \times 10^6$ units/dose (at 0.1 ml/nostril) were effective in conferring protection whereas doses at one-tenth or one-one hundredth of this had no detectable effect (Finter et al., op cit, p. 188). However, doses of about $1 \times 10^6$ units of interferon have been associated with annoying, mild nasal irritation and greater doses are markedly irritating (Finter et al. Id.).

Interferons also have been administered in the form of eyedrops to treat herpes simplex virus conjunctivitis and intravenously or intraperitoneally as injections or infusions for the treatment of various viral infections. Eyedrops typically contained greater than about $1 \times 10^6$ units of interferon/ml (one preparation containing 60,000 units/ml was reported to confer no clinical benefit; Sundmacher et al., 1976, "J. Infect. Dis." 133: A160–A164). Intravenous doses also generally exceeded $1 \times 10^6$ units/patient, although earlier workers constrained by the crude interferon preparations then available necessarily used lower doses. As a result of these studies, interferons generally are not believed to be as effective in treating established viral infections as they are in preventing them. Interferon preparations are needed that demonstrate enhanced activity towards active infections and that exhibit higher protective potency in order that lower interferon doses can be used.

Tumor necrosis factor (Pennica et al., 20/27 December 1984, "Nature" 312: 724) and lymphotoxin (Gray et al., 20/27 December 1984, "Nature" 312: 721) are proteins produced by activated macrophages and lymphocytes, respectively designated "TNF" and "LT" herein. They are described in copending U.S. Ser. No. 06/677,454 and 06/608,316. Both are directly cytotoxic to tumor cells in vitro and in vivo, and synergize with interferons in this respect (Lee at al., 1984, "J. Immun." 133: 1083). However, neither TNF nor LT per se are presently known to have any direct antiviral protective activity. For the effect of cytotoxic substances on virally infected cells see Eifel et al., "Cell. Imm.", 47: 197–203 (1979) and Aderka et al., "Cell. Imm." 92: 218–225 (1985).

It is an object of this invention to enhance the antiviral activity of interferons without increasing the incidence of interferon side effects.

It is a further object to enhance the antiviral specificity of interferons.

It is an additional object to employ interferons in the prophylaxis of individuals against viral infection, particularly infection by DNA viruses.

These and other objects of the invention will be apparent from the invention as a whole.

SUMMARY

The objects of this invention are accomplished by administering to a mammal previously infected or at risk from viral infection an antivirally effective amount of (a) an interferon and (b) a TNF or an LT. Notwithstanding the absence of any known antiviral protective activity by TNF or LT alone, TNF or LT synergistically enhance the antiviral activity of interferons. Typically, and quite unexpectedly, the activity of interferon is increased about from 2 to over 100 times by including TNF or LT in the interferon composition. The greatest effect is observed with gamma interferon.

Interferon compositions are provided that, at the time of this invention, would have been believed to contain inadequate interferon for therapeutic use, including either antiviral or antitumor uses. These interferon doses are less than about 500,000 International Units, generally less than 25,000 Units. They are rendered efficacious by the inclusion therein of LT or TNF in an amount in itself insufficient to demonstrate LT or TNF toxicity but sufficient for enhancing the antiviral activity of interferon.

DETAILED DESCRIPTION

Interferons are well known. In nature they comprise the β, γ and the about 20 different interferon-α subtypes. Their most relevant characteristic for the purposes herein is that they are capable of protecting cells in vitro and in vivo from viral infection. The interferons used in the process or composition of this invention typically are interferon-α, β or γ, with interferon-γ being preferred. Interferons produced in recombinant cell culture, from natural isolates or by stable untransformed cell lines are satisfactory for use herein, as are interferon amino acid sequence or glycosylation variants (including unglycosylated forms) so long as they exhibit anti-viral activity. Interferon-γ should be of the same animal species for which therapy is intended because interferon-γ is known to be species specific. The preferred interferon is human interferon-γ. The interferons desirably are substantially homogeneous and will have a specific activity in excess of about $1 \times 10^6$ International Units/mg.

TNF and LT include the products of recombinant or untransformed cell culture, including amino acid sequence or (in the case of LT) glycosylation variants (including unglycosylated LT). Suitable TNF and LT embodiments are described in copending U.S. Ser. No. 06/677,454 and 06/608,316. Either TNF or LT alone, or mixtures thereof, are suitable. Since TNF and LT are not species-specific in their ability to synergize with interferons, TNF or LT from one species is useful in the therapy of another. Preferably, human mature TNF or human unglycosylated mature LT are used herein.

The compositions herein include a pharmaceutically acceptable vehicle such as those heretofore used in the therapeutic administration of interferons, TNF or LT, e.g. physiological saline or 5% dextrose, together with conventional stabilizers and/or excipients. The compositions are provided lyophilized or as sterile aqueous solutions.

Several variables will be taken into account by the ordinary artisan in determining the appropriate proportion of interferon to TNF or LT to be used, the concentration of interferon, LT or TNF in the therapeutic compositions and the dosage to be administered. These include the animal species to be treated, the administration route, the interferon or mixture thereof selected, and the clinical condition of the patient (including the stage and degree of viral infection, if any, present at the commencement of treatment). Suitable doses of interferon ranging about from 50% to 0.1% of those heretofore believed to be the minimum effective doses are useful in conferring resistance to viral infection and for the killing of virally infected cells. These doses will range up to about 500,000 International Units/70 Kg patient, but are typically less than about 100,000 Units/70 Kg. The relative proportion by weight of interferon to TNF or LT generally ranges about from 1000:1 to 1:1, with about 100:1 being preferred. Therapeutic compositions typically are aqueous solutions containing about from $1 \times 10^3$ to $1 \times 10^5$ IU of interferon/ml and about from 1 ng to 5 μg of TNF or LT/ml. These are administered intranasally, intraperitoneally or intravenously, depending upon the viral infection to be interdicted or treated. Intranasal doses generally are less than about 25,000 International Units (in 0.1 ml volume), while intravenous doses are less than about 500,000, generally less than 100,000 Units.

The method and compositions of this invention are useful in preventing or treating active or latent infections by DNA viruses, single stranded RNA or double stranded RNA viruses, including without limitation adenoviruses, herpes virus, papovavirus (including simian virus 40, papilloma and polyoma viruses), pox viruses such as small pox and vaccina, arbovirus, arenovirus, coronavirus, myxovirus (New Castle disease, mumps, measles and respiratory synctial virus), rhinovirus, paramyxovirus such as influenza viruses A, B or C, parvovirus, picornavirus, togavirus, retrovirus (including HTLV-I, II and III), reovirus and rotavirus. Other specific viruses include rubella, herpes simplex, varicella-zoster, chicken pox, cytomegalovirus, ebola virus, rabies and hepatitis B.

The synergistic anti-viral protective effect of interferons together with TNF or LT is broadly applicable to all mammals. The cell lines shown in the following Table 1 were seeded into 24-well tissue culture plates and preincubated with TNF or LT plus interferon-γ. All were protected (as determined by cytopathic effect) to at least some degree against infection with EMC, VSV and HSV-2 at multiples if infectivity of 1, 1 and 100, respectively.

TABLE 1

| (A) | Human Cell Lines | (B) | Non-Human Cells |
|---|---|---|---|
| 1. | A549 (lung carcinoma) | 1. | 3T3 (mouse fibroblast) |
| 2. | HT-1080 (lung fibrosarcoma) | 2. | C127 (mouse epithelial cells) |
| 3. | Hela (cervical carcinoma) | 3. | Raw-264 (mouse macrophage) |
| 4. | T24 (bladder tumor) | 4. | Rat-1 (rat fibroblast) |
| 5. | HT29 (colon tumor) | 5. | NRK (normal rat kidney) |
| 6. | 7860 (renal tumor) | 6. | PK15 (pig cells) |
| 7. | ST486 (lymphoid cells) | 7. | MDBK (bovine cells) |
| 8. | R8226 (lymphoid cells) | | |

Accordingly, the method of this invention is useful for conferring protection against viral infections on mammals, including man, cattle, swine, fowl and horses. Patients may or may not be known to harbor tumors or malignancies.

The method of this invention is particularly useful in the prophylaxis of highly communicable viral infections that may occur in dense populations of agricultural animals, the foremost being New Castle disease in chickens and shipping fever in cattle. In contradistinction to vaccines, the compositions herein are effective against all viruses, notwithstanding mutations that may occur in the viral population that could render a vaccine ineffective, and can be administered with rapid protective effect upon the first sign of an epidemic outbreak—thereby obviating the need to vaccinate an entire population of animals.

The method also is useful in the prophylaxis of respiratory tract infections. Those at risk to exposure, e.g. those having a family member who has contracted a common cold, will administer interferon and TNF or LT for protection from infection. The most convenient route of administration for viruses transmitted in animals or man through the respiratory tract by intranasal spray or pledget. This treatment will use the known compositions and methods except that only a fraction of the interferon previously employed need be used and the therapeutic regimen includes the administration of TNF or LT. Intranasal preparations optionally include permeation enhancers such as bile acid salts or nonionic polyoxyethylene ethers. The formulations will contain the indicated doses of interferons and TNF or LT, mannitol or other stabilizers or excipients and 1% by weight enhancer in pH 7.4 phosphate buffer. Other suitable intranasal base formulations are described in U.S. Pat. No. 4,476,116, EP Nos. 127,535A, 122,036A, 111,841A, and 128,831A.

Most conveniently the interferon and TNF or LT are administered simultaneously. However, it is within the scope of the method herein to administer them separately in any order and, if desired, by different routes of administration. Typically, the interferon and TNF or LT are administered no greater than about 8 hours apart.

The invention will be more fully understood in the light of the following examples. The interferons were the products of recombinant bacterial cell culture and were purified to a specific activity of about $10^8$ units/mg. TNF and LT also were recombinant, and had a specific activity of about $5 \times 10^7$ units/mg.

EXAMPLE 1

LT or TNF Potentiates the Antiviral Activity of Human Interferon-γ

A549 cells were seeded at $2 \times 10^4$/well in 96-well flat-bottom trays (Falcon Plastics) for 24 hr prior to incubation with serially 2-fold diluted samples. The samples were dilutions of interferon-γ at the concentrations indicated in FIG. 1. The samples otherwise contained 0.1 μg/ml of TNF or LT in Dulbecco modified Eagle's (DME) medium supplemented with 5 percent heat-inactivated fetal calf serum (FCS), glutamine (2 mM); penicilin (100 U/ml), and streptomycin (100 μg/ml). Control samples contained (a) no interferon, TNF or LT, (b) TNF alone or (c) Lt alone. After 18 hr of incubation at 37° C., culture supernatants were replaced with fresh DME medium containing 2 percent fetal calf serum (but no interferon, TNF or LT) and EMC virus at a multiplicity of infection ("MOI", the ratio of infectious virus/cell) of 1. The cytopathic effect (CPE) was determined by staining the viable cells with crystal violet and the titer was quantitatively monitored using a microelisa autoreader (MR580, Dynatech) and further confirmed visually. The CPE antiviral titer is expressed as the reciprocal of the dilution found to inhibit 50 percent of cell cytopathy and was standardized against the international reference sample of human interferon-γ (No. Gg 23-903-530).

Figure 1:
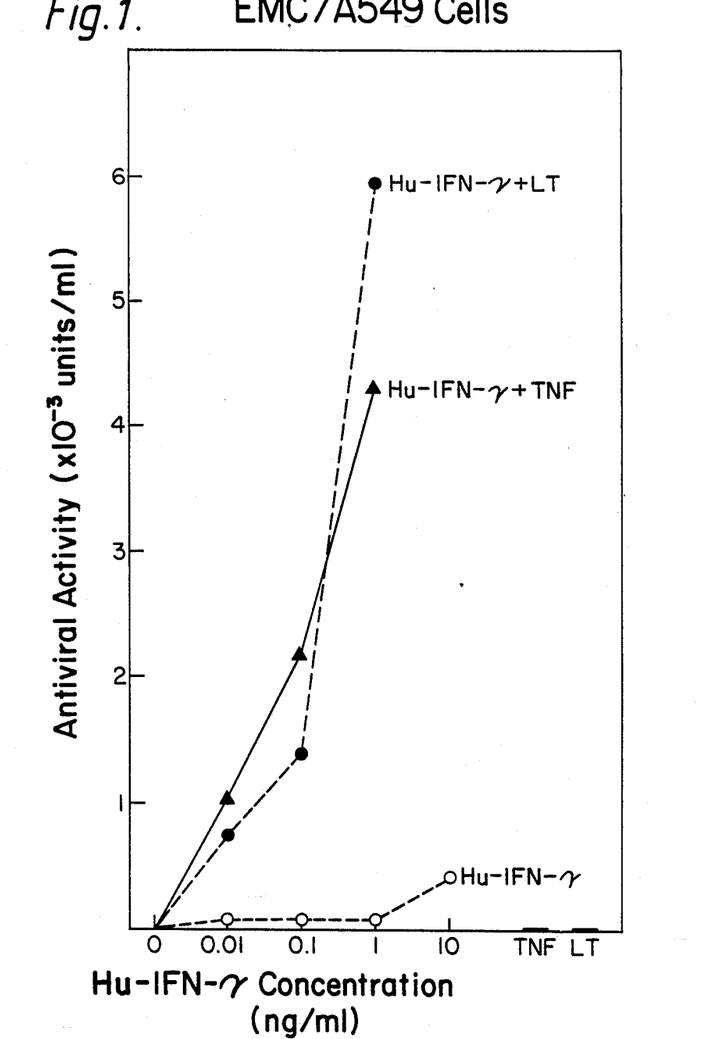
FIGS. 1 and 2 illustrate the dramatic increase in interferon-γ antiviral activity when interferon-γ is used in combination with LT or TNF.

As shown in FIG. 1, the presence of LT and TNF synergistically enhanced the anti-viral effect of interferon-γ at these interferon-γ concentrations. The anti-viral titers of interferon-γ increased greatly at concentrations above 1 ng/ml (data not shown). However, LT or TNF were very useful at conferring protection on target cells when interferon-γ was in itself present in low, largely ineffective concentrations.

EXAMPLE 2

Figure 2:
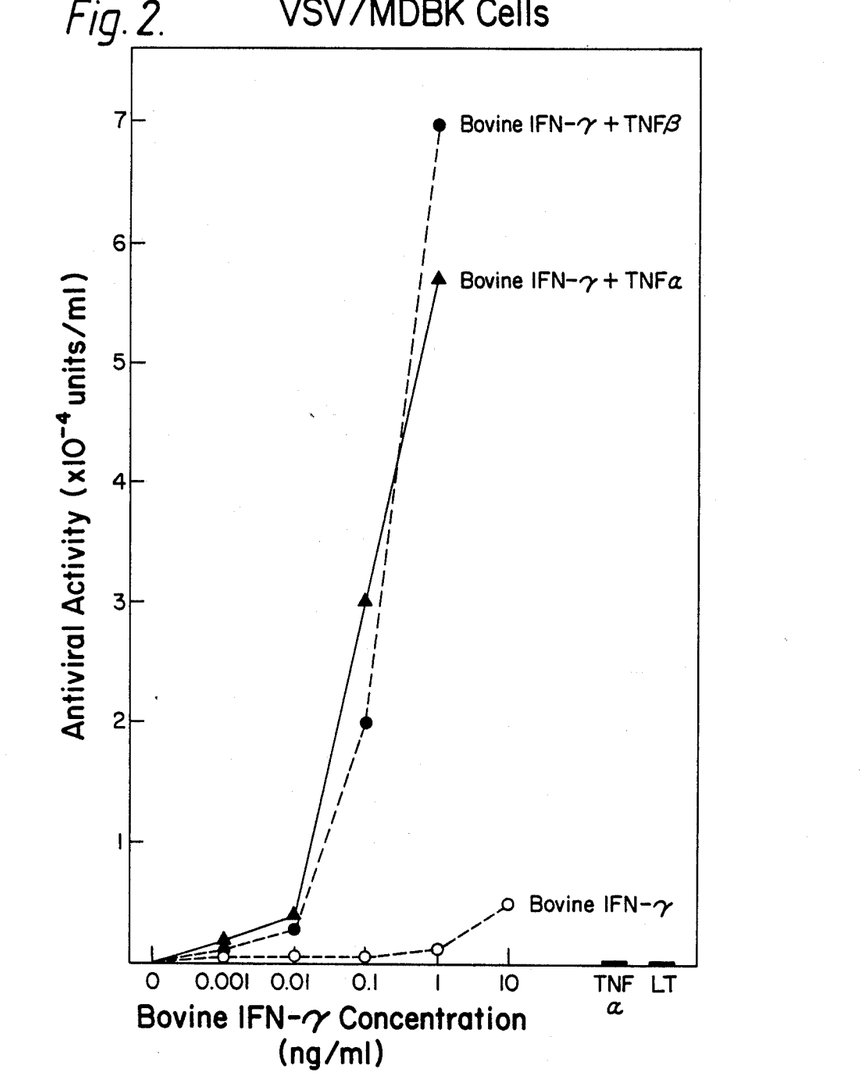

The Antiviral Activity of Bovine Interferon-γ is Enhanced by Human LT or TNF The method of Example 1 was repeated except that the TNF and LT concentrations were 1 μg/ml rather than 0.1 μg/ml, the interferon was bovine, the target cells were bovine MDBK and the virus was VSV. The results of the CPE assay are shown in FIG. 2. Once again, large increases in protection were enabled by the presence of TNF or LT. This data also shows that the species origin of the TNF or LT is unimportant for the protective effect and that it is applicable to other mammals than man.

EXAMPLE 3

Protection of A549 Cells from VSV Infection

Figure 3:
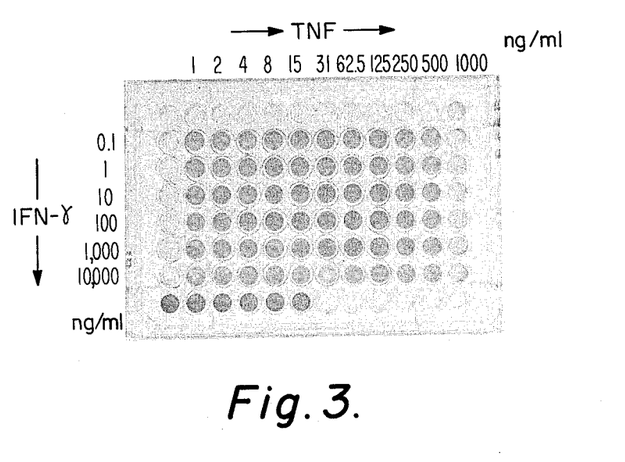
FIG. 3 depicts a cell culture which has been protected from viral infection by varying concentrations of TNF and interferon-γ.

The method of Example 1 was repeated except that the test virus was VSV and serial 10-fold and 2-fold dilutions of human recombinant interferon-γ and TNF respectively, starting with 1 μg/ml of TNF, and 10 μg/ml of interferon-γ. The results are shown in FIG. 3 as a cell culture plate that has been stained with crystal violet. Concentrations of interferon-γ ranging from 0.0001 to 10 μg were ineffective in protecting the cells, as were concentrations of TNF ranging downward from 1 μg/ml to 1 ng/ml. The virally infected and uninfected controls produced the expected results as shown. However, the combination of TNF and inteferon-γ protected the cells against VSV infection even at concentrations respectively ranging about from 1 μg/ml to 1 ng/ml and 10 μg/ml to 0.1 ng/ml.

EXAMPLE 4

Protective Enhancing Effect of TNF or LT on Interferons-α and β

Figure 4A:
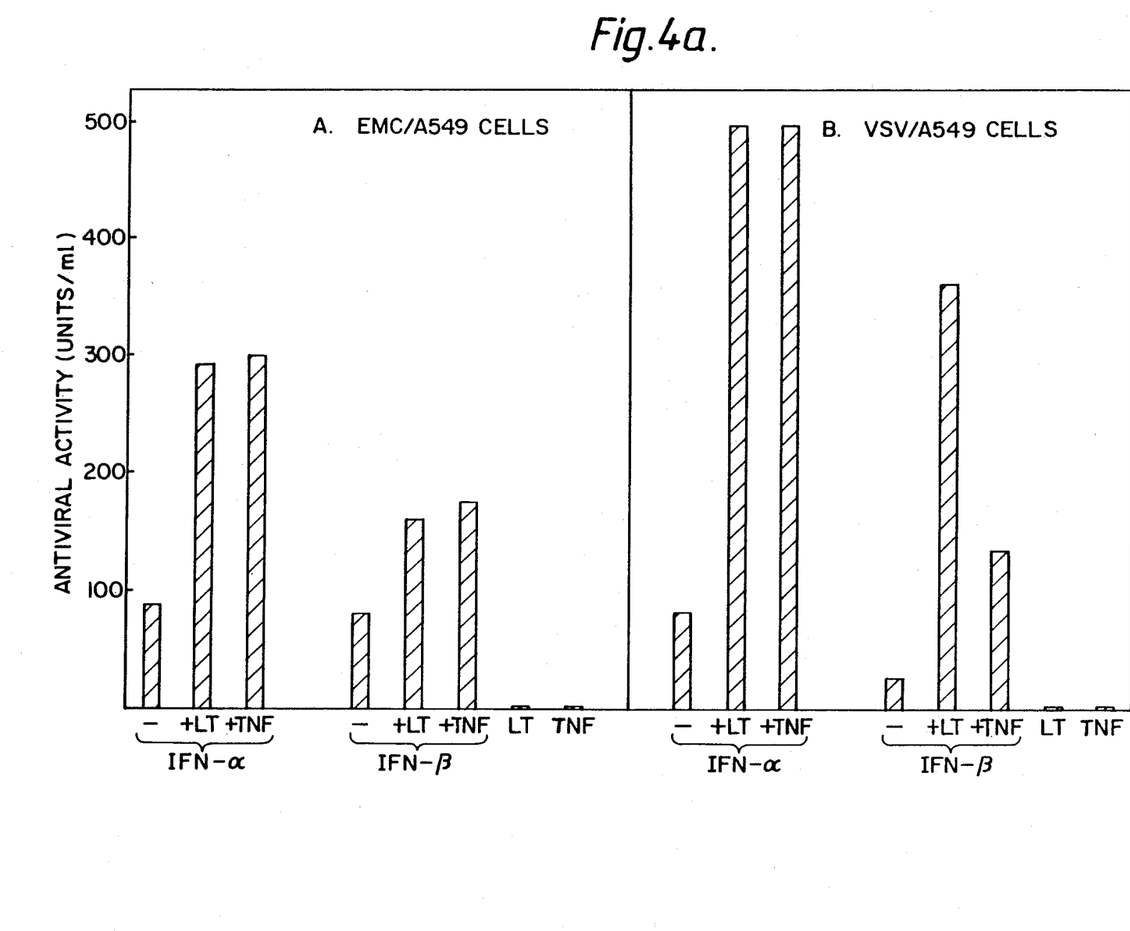
FIGS. 4a and 4b show that the antiviral activity of interferon-α, β or γ is enhanced by TNF or LT.
Figure 4B:
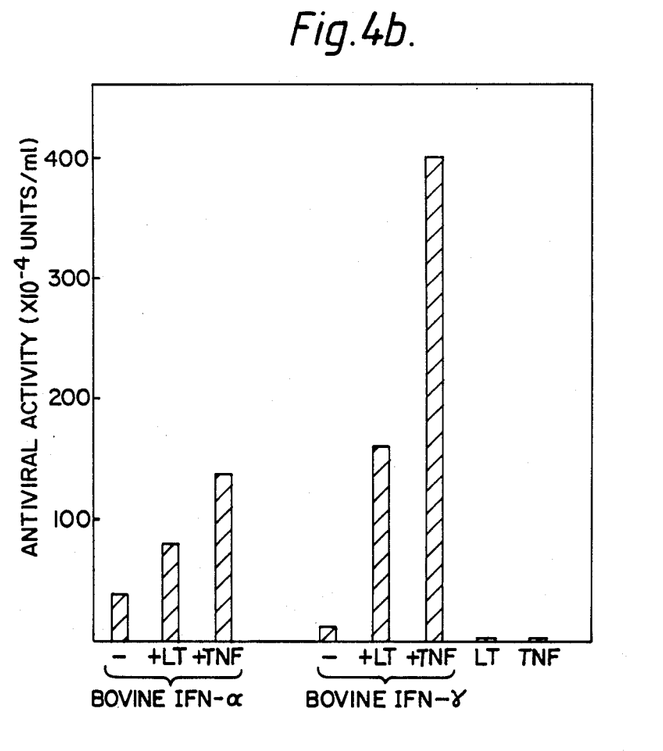
Figure 5A:
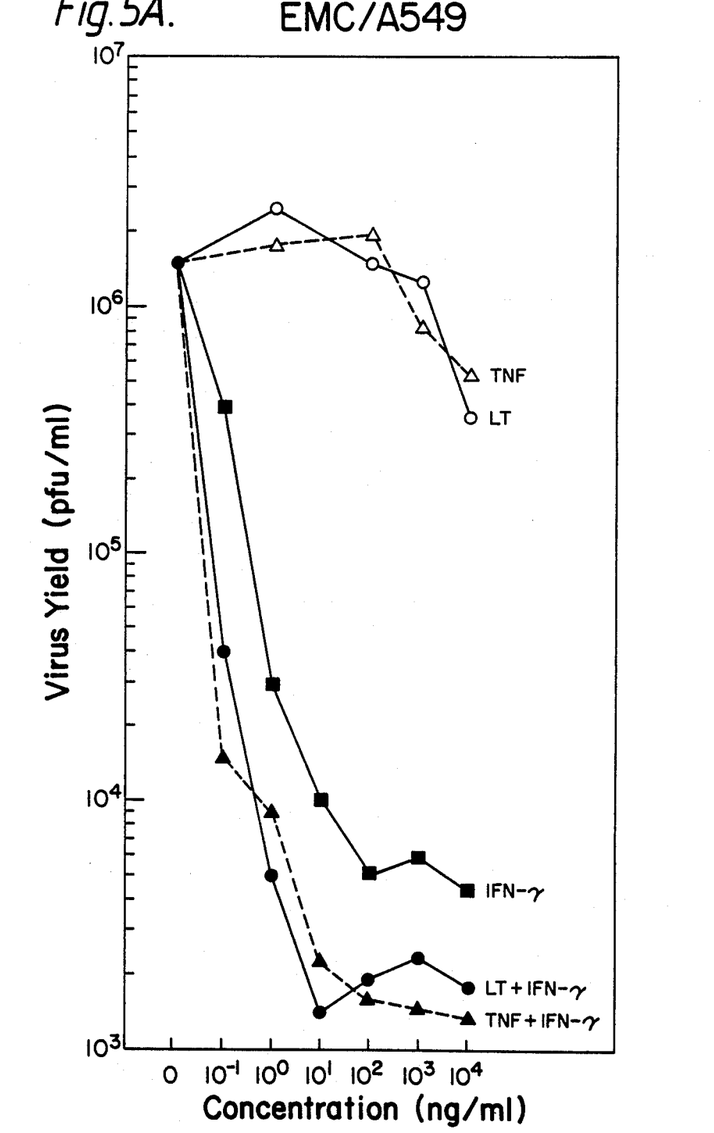
FIGS. 5a–5d illustrate that inhibition of viral replication by interferon-γ is potentiated by TNF or LT.
Figure 5B:
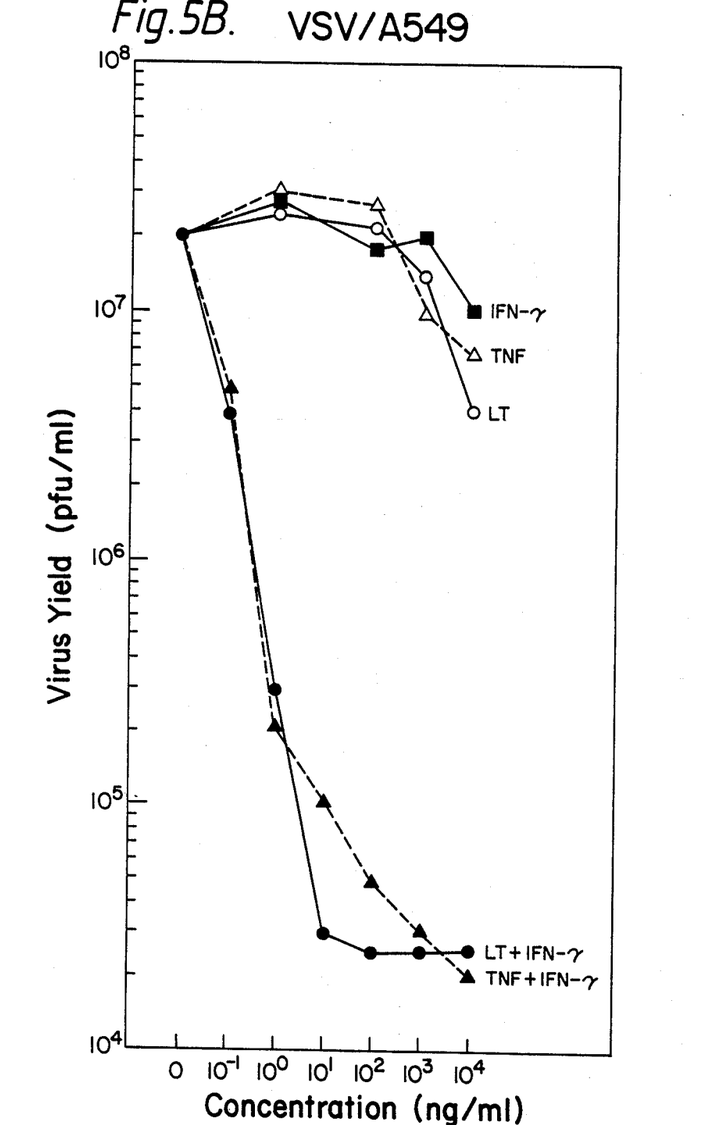
Figure 5C:
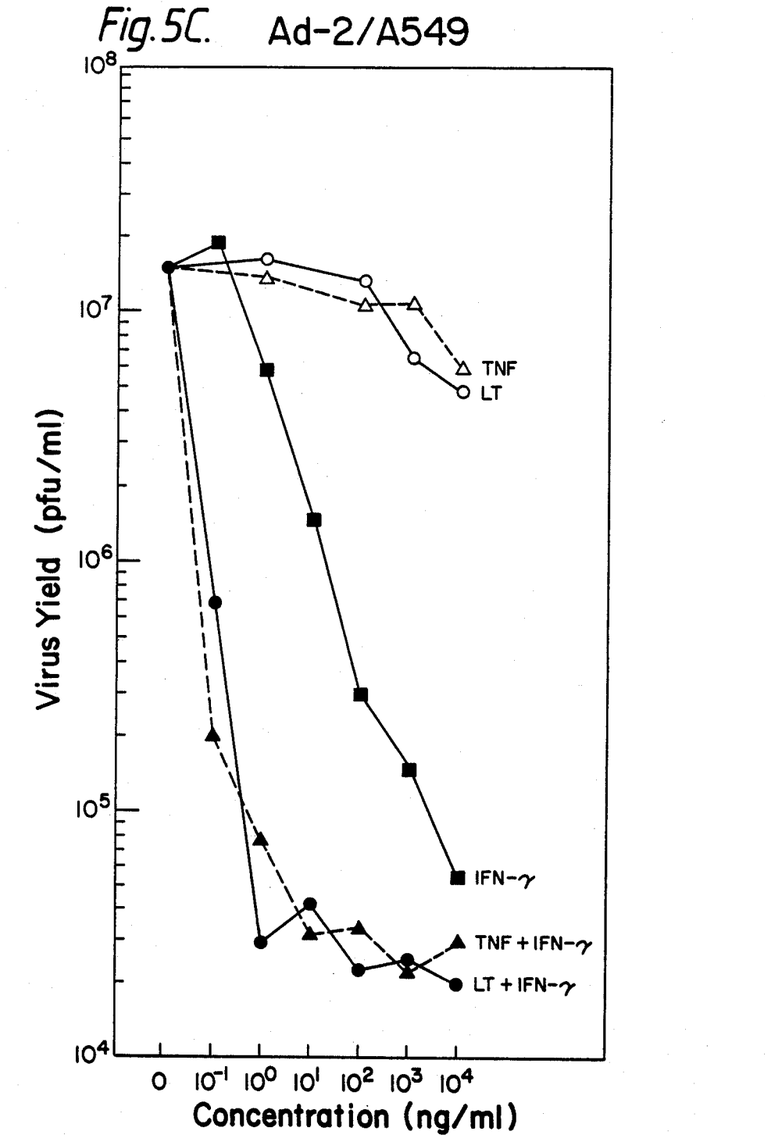
Figure 5D:
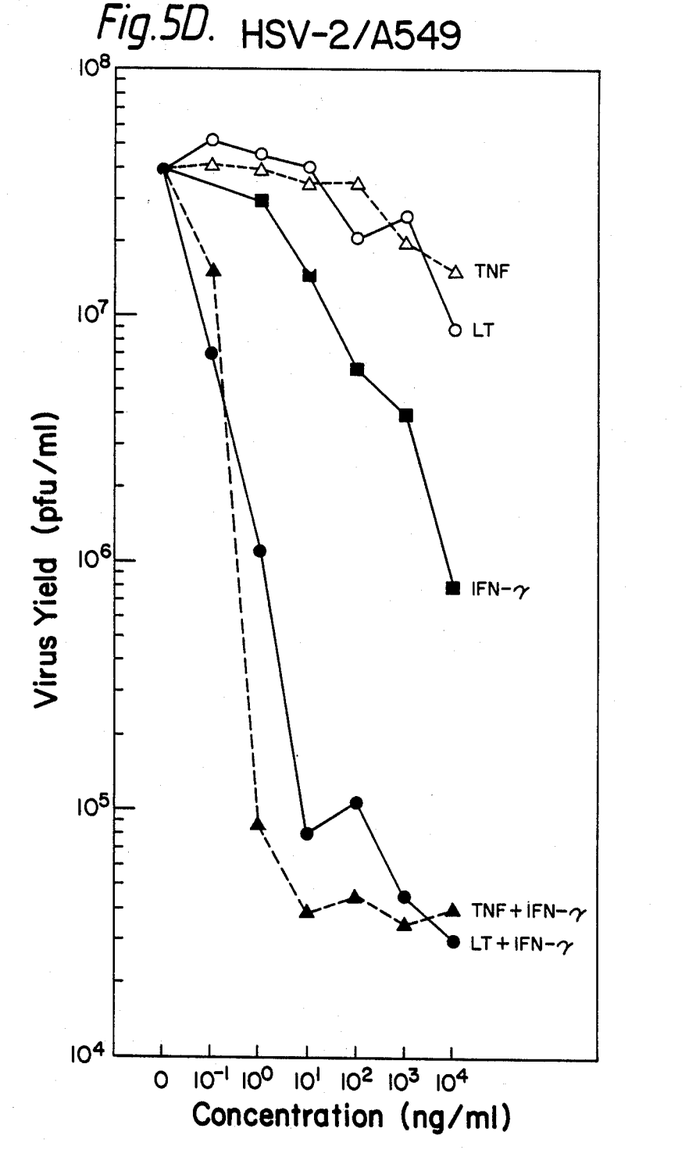

The method of Example 1 was repeated with EMC-/A549 as well as VSV/A549. The interferon concentrations were 10 ng/ml of interferon-α and 10 ng/ml of interferon-β. As shown in FIG. 4a, interferon-α and, to a lesser degree, interferon-β demonstrated antiviral synergy with human TNF or LT. Similar results were obtained with the MDBK/VSV and bovine interferon-α and γ as shown in FIG. 4b.

EXAMPLE 5

Synergistic Inhibition of Viral Replication

A549 cells were seeded into 24-well tissue culture plates (Costar) for 24 hr and then treated with various concentration of human LT, TNF or interferon-γ for 18 hr, and the medium removed before challenge with EMC, VSV, Adenovirus-2 (Ad-2) and Herpes Simplex-2 (HSV-2) viruses. The multiplicities of infection of EMC, VSV, Ad-2 and HSV-2 were 1, 1, 100 and 100, respectively. The concentration of TNF, LT and interferon-γ ranged from 0.1 ng/ml to 10 μg/ml. After an adsorption period of 2 hr, the supernatants were aspirated to remove the unadsorbed virus and the cells incubated at 37° C. in medium containing 5 percent FCS. After 24 hr, the cultures (cells together with medium) were frozen and thawed twice to lyse the cells and then centrifuged at 400 Xg for 10 min and the virus yield determined by plaque assay as described in Rager-Zisman et al., "Proc. Soc. Exp. Med." 142: 1174–1179 (1973). Serial dilutions of the lysate were added to confluent A549 cells and incubated for 2 hr at 37° C. The supernatant was aspirated and the cells were then overlaid with medium containing 5 percent FCS and 0.7 percent agarose. After 24–48 hr, the plaques were visualized by fixing with formaldehyde and staining with crystal violet. The virus yields in terms of plaque forming units/ml (PFU/ml) were determined and the results shown in FIGS. 5a–5d. These figures demonstrate synergistic enhancement of antiviral activity, particularly at low interferon-γ concentrations.

EXAMPLE 6

Synergistic Killing of Virally-Infected Cells

The method of Example 1 was repeated with VSV at an MOI of 10 and without preincubation with interferon, TNF or LT. VSV was incubated at 37° C. with the cells for 4 hours, after which the virus was washed from the infected cells. Then, the VSV-infected or uninfected cells were treated with 0.1 μg/ml of Lt, or interferon-γ, alone or in combination as shown in Table 2. After 12 and 18 hours at 37° C., the viability of the cells was determined by trypan blue or propidium iodide staining. The results are shown in Table 2 below.

TABLE 2

| Cell treatment | Viability Count (%) | | | |
|---|---|---|---|---|
| | Uninfected | | VSV-infected | |
| | 12 hr | 18 hr | 12 hr | 18 hr |
| control | ~100 | | 92 | 70 |
| LT | ~100 | | 41 | 29 |
| TNF | ~100 | | 38 | 31 |
| interferon-γ | ~100 | | 91 | 66 |
| LT + interferon-γ | ~100 | | 14 | 0 |
| TNF + interferon-γ | ~100 | | 12 | 0 |

Table 2 shows that virally infected cells were killed in synergistic fashion when combinations of interferon-γ and TNF or LT were used. Taken together with the results in previous Examples, this suggests that combinations of TNF or LT plus an interferon would act to counteract viral infections by two mechanisms: one by conferring protection on uninfected cells and the second by killing virally-infected cells.

I claim:

1. A method effective for the treatment or prophylaxis of a viral respiratory tract infection selected from the group consisting of New Castle Disease and shipping fever, comprising administering to a mammal previously infected or at risk from said viral infections an anti-virally effective amount of (a) interferon and (b) tumor necrosis factor (TNF) or lymphotoxin (LT).

2. The method of claim 1 wherein the interferon is interferon-γ.

3. The method of claim 1 wherein the interferon is a human interferon.

4. The method of claim 1 wherein the anti-virally effective amount of interferon is about 100,000 International Units.

5. The method of claim 1 wherein the interferon and TNF or LT are administered simultaneously.

6. The method of claim 1 wherein the interferon and TNF or LT are administered intranasally.

7. The method of claim 1 wherein the interferon and TNF or LT are substantially pure products of recombinant cell culture.

8. The method of claim 1 wherein the infection is shipping fever.

* * * * *